(12) United States Patent
Wentland et al.

(10) Patent No.: US 7,057,035 B2
(45) Date of Patent: Jun. 6, 2006

(54) N-HYDROXYSUCCINIMIDE PROCESS FOR CONVERSION OF PHENOLS TO CARBOXAMIDES

(75) Inventors: Mark P. Wentland, Menands, NY (US); Rongliang Lou, Cheshire, CT (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 11/035,750

(22) Filed: Jan. 14, 2005

(65) Prior Publication Data

US 2005/0215799 A1 Sep. 29, 2005

Related U.S. Application Data

(63) Continuation of application No. PCT/US03/20882, filed on Jul. 2, 2003.

(60) Provisional application No. 60/396,047, filed on Jul. 16, 2002.

(51) Int. Cl.
*C07D 487/08* (2006.01)
*C07D 221/28* (2006.01)
*C07D 207/46* (2006.01)

(52) U.S. Cl. .......................... 540/477; 546/74; 548/542

(58) Field of Classification Search ................. 540/477; 546/74; 548/542
See application file for complete search history.

(56) References Cited

U.S. PATENT DOCUMENTS 5,734,064 A 3/1998 Pochlauer et al. .......... 548/542
6,376,230 B1 4/2002 Aikins et al. ............... 435/280

OTHER PUBLICATIONS

Lou et al., "Preparation of N-hydroxysuccinimido esters via palladium-catalyzed carbonylation of aryl triflates and halides," Tetrahedron Letters, Elsevier Science Publishers, 44(12) pp. 2477-2480 (2003).
Wentland et al., "8-Carboxamidocyclazocine Analogues: Redefining the Structure-Activity Relationships of 2,6-Methano-3-benzazocines," Bioorganic & Medicinal Chemistry Letters, 11(5) pp. 623-626 (2001).

*Primary Examiner*—Kamal A. Saeed
*Assistant Examiner*—Jason M. Nolan
(74) *Attorney, Agent, or Firm*—Heslin Rothenberg Farley & Mesiti, P.C.

(57) ABSTRACT

A process for converting an aryl triflate, heteroaryl triflate, aryl halide or heteroaryl halide to an N-hydroxysuccinimido ester is disclosed. The process involves reacting the triflate or halide with carbon monoxide and N-hydroxysuccinimide in a solvent in the presence of a palladium catalyst and a base.

10 Claims, No Drawings

N-HYDROXYSUCCINIMIDE PROCESS FOR CONVERSION OF PHENOLS TO CARBOXAMIDES

"CROSS REFERENCE TO RELATED APPLICATION"

This application is a continuation of PCT/US03/20882 filed Jul. 2, 2003 and published as WO 2004/007449 on Jan. 22, 2004 and claims priority from U.S. Provisional Patent Application 60/396,047 filed Jul. 16, 2002, the disclosures of which are incorporated by reference in their entirety.

STATEMENT AS TO RIGHTS UNDER FEDERALLY-SPONSORED RESEARCH

This invention was made with Government support under Contract No. DA 12180 awarded by the National Institute on Drug Abuse. Accordingly, the U.S. Government may have certain rights in this invention.

FIELD OF THE INVENTION

The invention relates to a process for converting phenols to amides via N-hydroxysuccinimide esters.

BACKGROUND OF THE INVENTION

Carboxylic acid esters of N-hydroxysuccinimide (NHS) have been widely used in organic synthesis as reactive acylating reagents (a.k.a. active esters). These active esters are especially useful as intermediates in the synthesis of peptides and proteins via N-acylation. The chemistry of N-hydroxysuccinimido esters has been reviewed Cline et al [*J. Am. Chem. Soc.* 1987, 109, 3087–3091] and by Hirata et al. [*Yukagaku* 1991, 40, 1088–1094]. These and all other patents and literature references cited in this application are incorporated herein by reference. The classical methods for making N-hydroxysuccinimido esters include (a) the reaction of the sodium, potassium, silver or thallium salt of N-hydroxysuccinimide with an acyl chloride; (b) esterification of a carboxylic acid with NHS in the presence of a carbodiimide; (c) esterification of a carboxylic acid with NHS in the presence of azodicarboxylate/triphenylphosphine; (d) reaction of bis(N-succinimidyl) carbonate with carboxylic acid; and (e) acylation of NHS with mixed anhydrides. The processes of the art commonly begin with a carboxylic acid, convert it to an N-hydroxysuccinimido ester, and react the N-hydroxysuccinimido ester with an amine to provide an amide.

The recent publication [PCT application WO 02/36573] of amide bioisosteres of 8-hydroxy-2,6-methano-3-benzazocines and 3-hydroxymorphinanes has stimulated interest in methods for direct conversion of phenols to amides. Such a process would be useful for producing compounds having activity as analgesics, anti-pruritics, anti-diarrheal agents, anticonvulsants, antitussives, anorexics and as treatments for hyperalgesia, drug addiction, respiratory depression, dyskinesia, pain (including neuropathic pain), irritable bowel syndrome and gastrointestinal motility disorders.

SUMMARY OF THE INVENTION

The invention relates to a process for synthesizing an N-hydroxysuccinimido ester 2 in one step from readily available starting materials, namely aryl triflates or halides (1).

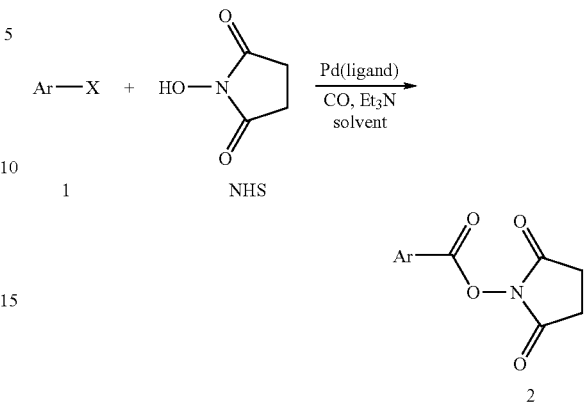

Scheme 1.

In this first aspect, the invention relates to a process for converting an aryl triflate, heteroaryl triflate, aryl halide or heteroaryl halide to an N-hydroxysuccinimido ester. The process involves reacting the triflate or halide with carbon monoxide and N-hydroxysuccinimide in a solvent in the presence of a palladium catalyst and a base.

The process can be used to convert a phenol or hydroxyheteroaryl compound to an N-hydroxysuccinimido ester by the additional step of:
(a) first, converting the phenol or hydroxyheteroaryl compound to an aryl triflate, heteroaryl triflate, aryl halide or heteroaryl halide; and
(b) then, reacting the triflate or halide with carbon monoxide and N-hydroxysuccinimide in a solvent in the presence of a palladium catalyst and a base.

The process can also be used to convert a phenol or hydroxyheteroaryl compound to a carboxamide via the succinimide ester by the additional step of reacting the aryl or heteroaryl N-hydroxysuccinimido ester with an amine to provide an amide.

DETAILED DESCRIPTION OF THE INVENTION

The invention relates to a novel and convenient method (Scheme 1) for the preparation of N-hydroxysuccinimido esters 2 of aromatic carboxylic acids directly from aryl triflates or aryl halides, particularly iodides, under Pd-catalyzed carbonylation conditions. We have found that the optimal palladium catalyst is palladium complexed with a ligand chosen from BINAP [2,2'-bis (diphenylphosphino)-1,1'-binaphthyl]; DPPF [1,1'-bis (diphenylphosphino)ferrocene]; DPPP [1,3-bis(diphenylphosphino)-propane]; PPh₃; DCPE [1,2-bis(dicyclohexylphosphino)ethane] and Xantphos [4,5-bis (diphenylphosphino)-9,9'-dimethylxanthene]. Of these, Xantphos is preferred. The optimal amount of catalyst appears to be 2 to 10 mol %. The preferred base is a tertiary amine. We have employed triethylamine, but tertiary amines (e.g diisopropylethylamine, N-methylmorpholine, etc.) would work. As the solvent, any solvent known to be useful for palladium-catalyzed reactions would work; preferably the solvent is DMSO, DMF, dioxane, THF, toluene or mixtures thereof. DMSO is most preferred.

The following is the general procedure used to make N-succinimidyl 2-naphthoate (4) (Table 1, Entry 1):

Scheme 2.

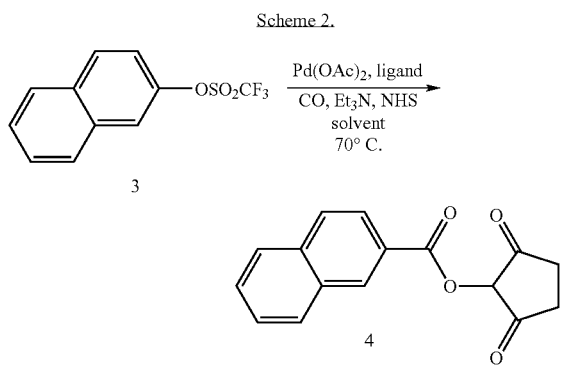

DMSO and triethylamine were degassed by the way of three freeze-thaw cycles and N-hydroxysuccinimide was dried over $P_2O_5$ in vacuum for 24 h. Under argon atmosphere, triethylamine (0.31 mL, 2.25 mmol) was added to a mixture of 2-naphthyl triflate (414.0 mg, 1.5 mmol), [prepared according to Echavarren et al. *J. Am. Chem. Soc.* 1987, 109, 5478–5486], palladium acetate (16.8 mg. 0.075 mmol), Xantphos (43.4 mg, 0.075 mmol) and N-hydroxysuccinimide (241.5 mg, 2.1 mmol) in DMSO (2 mL). The solution was purged with carbon monoxide for 15 min and stirred under a CO balloon at 70° C. for 17 hours. The reaction mixture was then cooled to room temperature, diluted with 20 mL of ethyl acetate and washed with saturated sodium bicarbonate solution and water. The organic phase was dried over sodium sulfate and evaporated to give crude product. Chromatography on silica gel using hexane:acetone (4:1) provided 381.3 mg (94%) N-hydroxysuccinimidyl 2-naphthoate as a white crystalline solid.

We explored the parameters for this conversion using 3, the triflate ester of 2-naphthol. The palladium source [Pd(OAc)$_2$] and the base [Et$_3$N] were held constant. The temperature and pressure of the carbon monoxide were held at 1 atmosphere CO at 70° C. As shown in Scheme 2, we varied the Pd ligand (Xantphos, DPPF, DPPP, BINAP, DCPE, and PPh$_3$), solvent (DMSO, DMF, toluene and dioxane), and stoichiometry. For the conversion of 3 to the corresponding active ester 4, we observed that an excellent yield of 94% could be realized using Xantphos (5 mol %) as Pd ligand with a 1:1.4:1.5 molar ratio of 3:NHS:Et$_3$N in DMSO for 17 hours. The success of this reaction was not highly dependent on time, in that tlc showed little starting material after 5 hours and little or no product decomposition after 24 hours.

Using similar conditions, we found that when Xantphos was replaced with the following well-known Pd ligands, lower yields for this conversion were realized: BINAP (32%), DPPF (40%), DPPP (72%), PPh$_3$ (no reaction with triflate up to 10 mol %) or DCPE (no reaction with triflate up to 10 mol %). Besides the desired product 4 (when formed), the reaction mixtures for these examples contained either starting material or unknown by-products. We also found that the choice of solvent affected the yield. When 3 was subjected to the optimized conditions, replacing DMSO with other solvents known to be useful in Pd catalyzed reactions had the following effect on yield: DMF (59%), dioxane (90%), THF (63%), and toluene (61%).

The effects of the amount of Pd ligand and molar ratio of 3:NHS:Et$_3$N were also examined. When 2.5 mol % Xantphos was used versus the 5 mol %, the yield of product decreased from 94% to 80%. Likewise, when the ratio of 3:NHS:Et$_3$N was varied from the optimized 1:1.4:1.5 ratio to, for example, 1:1.05:1.2, 1:1.4:3.0, and 1:2.5:1.5, the yields decreased to 87%, 74%, and 51%, respectively. From the experiments, it appears that, although there are optimal conditions, considerable variation in ligand, solvent and stoichiometry is possible.

We also studied the potential generality of the reaction by varying the nature of the aromatic group (Ar) and leaving group (X) of the substrate. Results are summarized in Table 1. Using X=OTf and the optimized conditions identified for Ar=2-naphthyl, (Entry 1) we found that many triflates reacted with carbon monoxide and NHS smoothly to give rise to the corresponding esters in very good yields. We also studied the effect of variation of the leaving group by evaluating iodobenzene (Entry 14) and bromobenzene (Entry 23) as substrates in the reaction. Replacing the triflate of PhOTf with iodo has a positive effect, with the yield increasing from 72% (Entry 3) to 86% (Entry 14). However, using bromine as leaving group does not appear advantageous. When a variety of functional groups were introduced into iodobenzene, all substrates evaluated (Entries 15–22) gave very good results. Relative to the corresponding triflates or bromides, aryl iodides appear to undergo the Pd-catalyzed carbonylation faster and in higher yields.

TABLE 1

Preparation of N-Hydroxysuccinimido Esters via Pd-Catalyzed Carbonylation of Aryl Triflates and Aryl Halides

| Entry | Ar | X | Yield (%)[a] |
|---|---|---|---|
| 1 | 2-naphthyl | OTf | 94 |
| 2 | 1-naphthyl | OTf | 88 |
| 3 | C$_6$H$_5$ | OTf | 72 |
| 4 | 3-pyridinyl | OTf | ND[b] |
| 5 | 4-Me—C$_6$H$_4$ | OTf | 66 |
| 6 | 3-Me—C$_6$H$_4$ | OTf | 88 |
| 7 | 2-Me—C$_6$H$_4$ | OTf | 47 |
| 8[d] | 3, 4-Me$_2$—C$_6$H$_4$ | OTf | 93 |
| 9[d] | 5, 6, 7, 8-H$_4$-2-naphthyl | OTf | 91 |
| 10 | 4-MeO—C$_6$H$_4$ | OTf | 57 |
| 11 | 4-NO$_2$—C$_6$H$_4$ | OTf | ND[b] |
| 12 | 4-Cl—C$_6$H$_4$ | OTf | ND[b] |
| 13[d] | 4-Cl-3-Me—C$_6$H$_4$ | OTf | 84 |
| 14 | C$_6$H$_5$ | I | 86 |
| 15 | 4-MeO—C$_6$H$_4$ | I | 85 |
| 16 | 4-NO$_2$—C$_6$H$_4$ | I | 73 |
| 17 | 4-CN—C$_6$H$_4$ | I | 93 |
| 18 | 4-Cl—C$_6$H$_4$ | I | 90 |
| 19 | 2-Me—C$_6$H$_4$ | I | 92 |
| 20 | 3-MeO-4-MeOCO—C$_6$H$_4$ | I | 72 |
| 21 | 3-pyridinyl | I | 61 |
| 22[c] | 2-thienyl | I | 83 |
| 23 | C$_6$H$_5$ | Br | 26 |
| 24 | 4-MeO—C$_6$H$_4$ | Br | No reaction |
| 25 | 4-NO$_2$—C$_6$H$_4$ | Br | ND[d] |

TABLE 1-continued

Preparation of N-Hydroxysuccinimido Esters via
Pd-Catalyzed Carbonylation of
Aryl Triflates and Aryl Halides

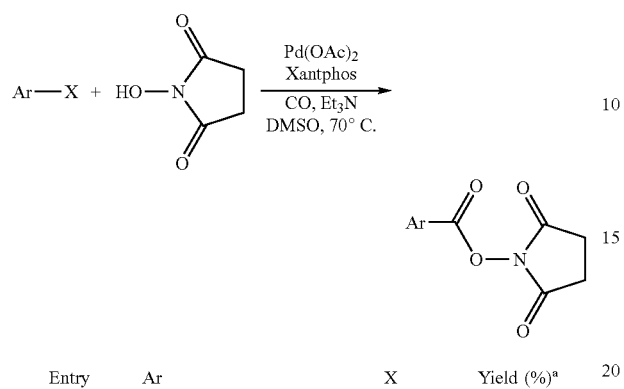

| Entry | Ar | X | Yield (%)[a] |
|-------|----|----|--------------|

[a] Isolated yields after purification by flash column chromatography. Spectroscopic data (IR, ¹H-NMR, MS) were in agreement with the assigned structures.
[b] Product formation Not Detectable (ND); only the corresponding phenol was observed in the reaction mixture.
[c] New compounds gave satisfactory element analysis.
[d] 28% of 4-nitrobenzoic acid was isolated as a by-product.

The triflate of cyclazocine, prepared by the method of Wentland et al., [*Bioorgan. Med. Chem. Lett.* 9,183–187 (2000)], was converted to the corresponding N-hydroxysuccinimido ester by the process of the invention as described above:

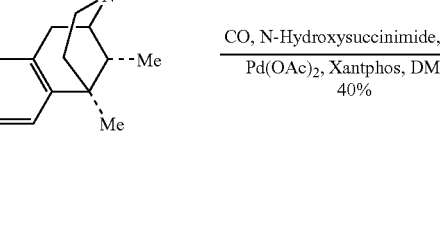

The N-hydroxysuccinimide esters were converted to amides by the following precedures:

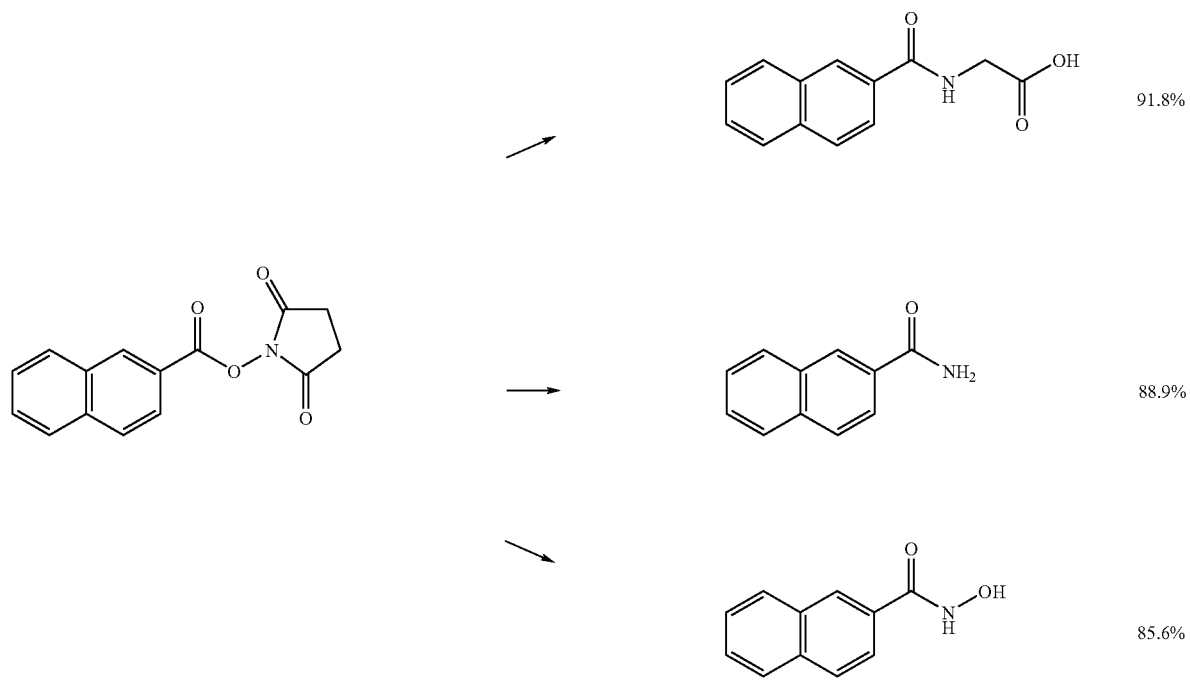

-continued
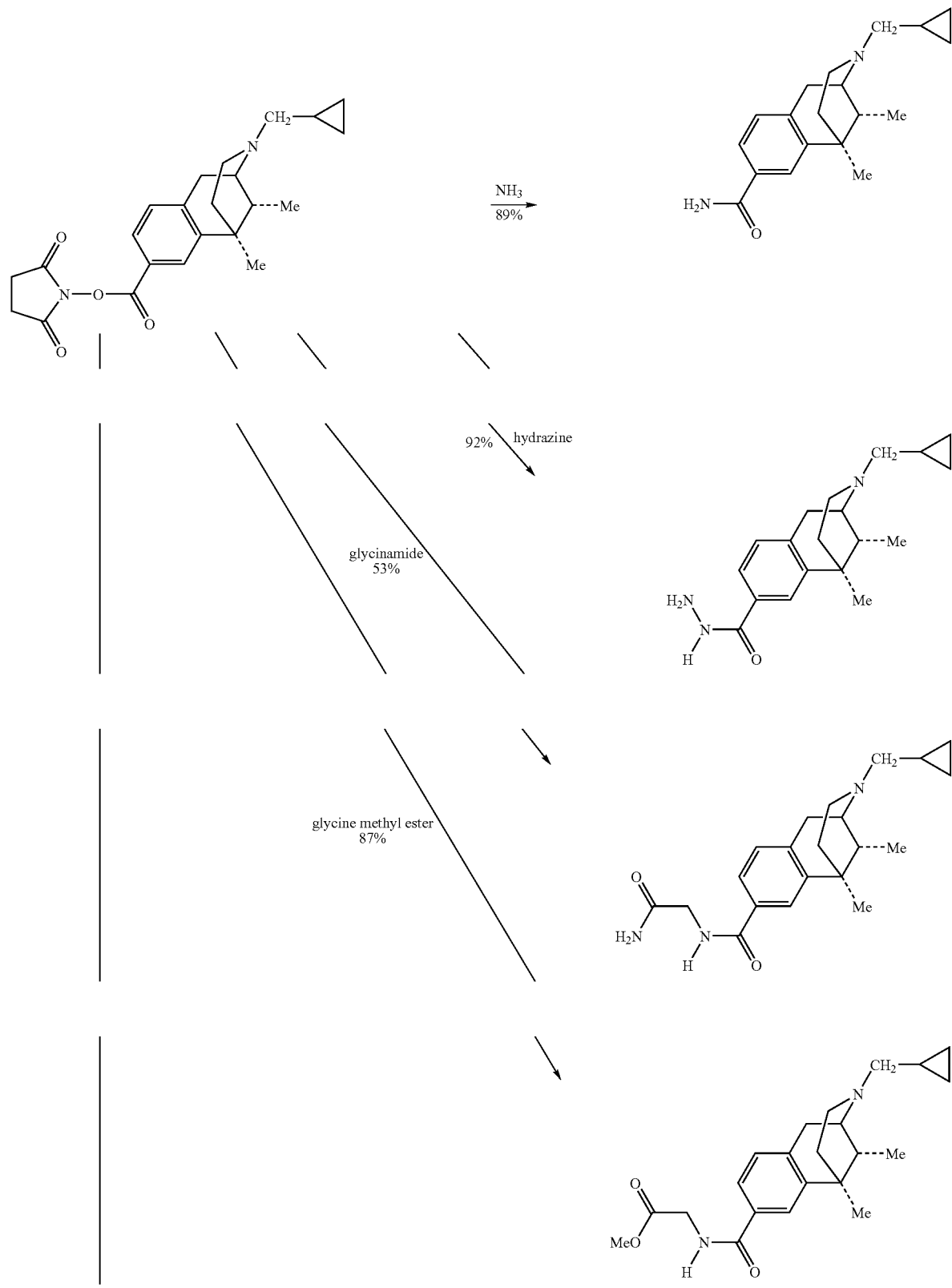

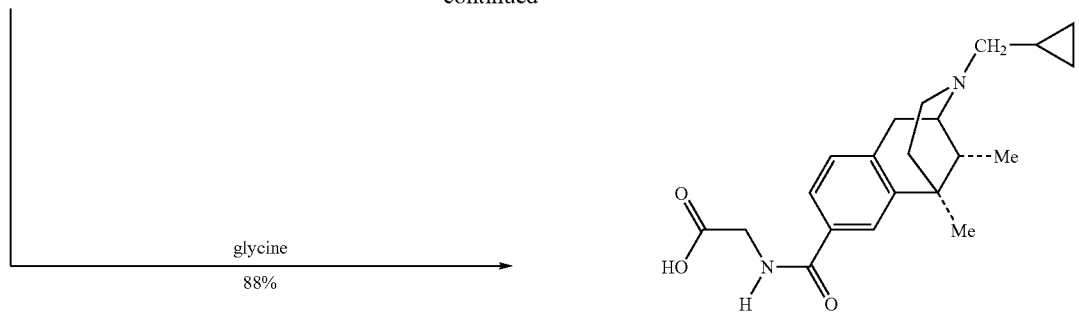

glycine
88%

General Method 1:

A mixture of 0.090 g "NHS-active ester of cyclazocine", 1 mL concentrated ammonium hydroxide and 2 mL $CH_2Cl_2$ was stirred at room temperature for 3 hours. The mixture was filtered and the filtrate was concentrated in vacuum to give a crude product that was purified by flash column chromatography (silica gel, $CH_2Cl_2$:MeOH:$NH_4OH$/25:1:0.1) give 0.068 g (89%) of 3-(cyclopropylmethyl)-1,2,3,4,5,6-hexahydro-cis-6,11-dimethyl-2,6-methano-3-benzazocine-8-carboxamide whose tlc and spectral properties were identical to previously reported material (Wentland et al., *Bioorganic & Medicinal Chemistry Letters* (2001), 11(5), 623–626.)

In similar fashion, 0.050 g of "NHS-active ester of cyclazocine" was treated with hydrazine hydrate to give a 92% yield of the corresponding hydrazoic acid derivative.

General Method 2:

A mixture of 0.110 g of "NHS-active ester of cyclazocine", 0.045 g glycinamide hydrochloride, 0.040 g of triethylamine, 1 mL of dioxane and 1 mL of water was stirred at room temperature for 1 h. The mixture was filtered and the filtrate was concentrated in vacuum to give material that was dissolved in $CH_2Cl_2$ and washed with water. After concentrating the $CH_2Cl_2$ solution, the crude product was purified by flash column chromatography (silica gel, $CH_2Cl_2$:MeOH:$NH_4OH$ 10:1:0.1) give 53% of the desired product, N-[2-acetamido]-3-(cyclopropylmethyl)-1,2,3,4,5,6-hexahydro-cis-6,11-dimethyl-2,6-methano-3-benzazocine-8-carboxamide, as a foam. Spectral properties and elemental analysis data ($C_{21}H_{29}N_3O_2 \cdot H_2O$, calculated C, 67.53, 8.37, 11.25; found: C, 67.54, H 8.16, N, 10.96) were consistent with the assigned structure.

In similar fashion, "NHS-active ester of cyclazocine" was treated with glycine hydrochloride and glycine methyl ester hydrochloride to give the corresponding $CH_2CO_2H$ and $CH_2CO_2Me$ derivatives, respectively, of 3-(cyclopropylmethyl)-1,2,3,4,5,6-hexahydro-cis-6,11-dimethyl-2,6-methano-3-benzazocine-8-carboxamide.

Phenols of interest, such as 8-hydroxy-2,6-methano-3-benzazocines and 3-hydroxymorphinanes, may be converted to triflates by reaction with trifluoromethanesulfonic anhydride in the presence of a base (e.g. pyridine). The reaction is well known in the art. Phenols of interest, such as 8-hydroxy-2,6-methano-3-benzazocines and 3-hydroxymorphinanes, may be converted to iodides by: (1) conversion to the triflate as described, (2) displacement of the triflate by boron as described by Nakamura et al. [*J. Org. Chem.* 1998, 63, 7529–7530] followed by (3) displacement of the boron by iodine, either from iodosuccinimide according to the method of Thiebes et al. [*Synlett,* 1998, 141–142] or from sodium iodide according to the method of Kabalka et al., [*Org. Prep. Proced Int.* 1982, 14, 359–62].

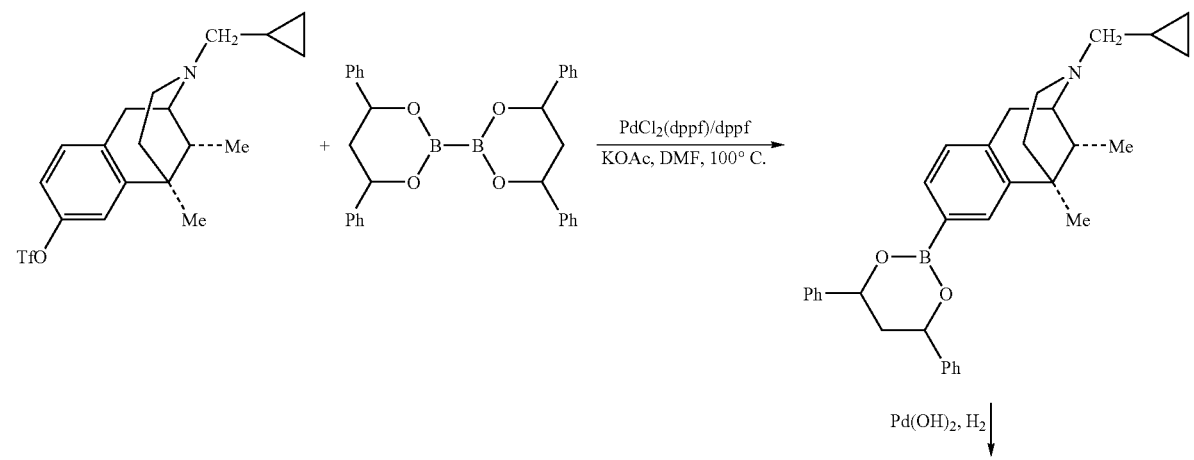

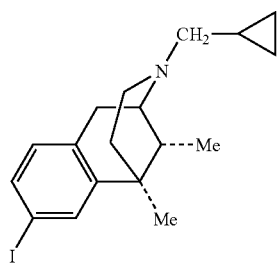

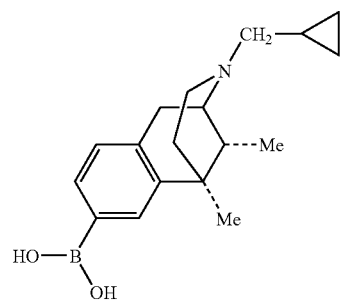

The invention claimed is:

1. A process for converting an aryl triflate or heteroaryl triflate to an N-hydroxysuccinimido ester comprising reacting said triflate with carbon monoxide and N-hydroxysuccinimide in a solvent in the presence of a palladium catalyst and a base.

2. A process for converting a phenol or hydroxyheteroaryl compound to an N-hydroxysuccinimido ester comprising:
   (a) converting said phenol or hydroxyheteroaryl compound to an aryl triflate or heteroaryl triflate; and
   (b) reacting said triflate with carbon monoxide and N-hydroxysuccinimide in a solvent in the presence of a palladium catalyst and a base.

3. A process for converting a phenol or hydroxyheteroaryl compound to an amide comprising:
   (a) converting said phenol or hydroxyheteroaryl compound to an aryl triflate or heteroaryl triflate;
   (b) reacting said triflate with carbon monoxide and N-hydroxysuccinimide in a solvent in the presence of a palladium catalyst and a base to provide an aryl or heteroaryl N-hydroxysuccinimido ester; and
   (c) reacting said aryl or heteroaryl N-hydroxysuccinimido ester with an amine to provide said amide.

4. A process according to claims 1 wherein said palladium catalyst is palladium complexed with a ligand chosen from BINAP [2,2'-bis(diphenylphosphino)-1,1'-binaphthyl]; DPPF [1,1'-bis(diphenylphosphino)ferrocene]; DPPP [1,3'-bis(diphenylphosphino)propane]; PPh$_3$; DCPE[1,2-bis(dicyclohexylphospino)ethane] and Xantphos [4,5-bis(diphenylphosphino)-9,9'-dimethylxanthene].

5. A process according to claim 4 wherein said catalyst is present in from 2 to 10 mol %.

6. A process according to claim 1 wherein said base is a tertiary amine.

7. A process according to claim 1 wherein said solvent is chosen from the group consisting of DMSO, DMF, dioxane, THF, toluene and mixtures thereof.

8. A process according to claim 2 wherein said phenol or hydroxyheteroaryl compound is reacted with trifluoromethanesulfonic anhydride in the presence of a base to provide said aryl triflate or heteroaryl triflate.

9. A process according to claim 8 wherein said aryl triflate or heteroaryl triflate is reacted with palladium and a borate reagent followed by iodide to provide an aryl iodide or heteroaryl iodide.

10. A process according to claim 2 wherein said phenol is an 8-hydroxy-2,6-methano-3-benzazocine or a 3-hydroxymorphinane.

* * * * *